United States Patent [19]
Tinney et al.

[11] 4,124,577
[45] Nov. 7, 1978

[54] NONAPEPTIDES AND METHODS FOR THEIR PRODUCTION

[75] Inventors: Francis J. Tinney; Elizabeth A. Lunney; Ernest D. Nicolaides, all of Ann Arbor, Mich.

[73] Assignee: Warner-Lambert, Morris Plains, N.J.

[21] Appl. No.: 805,765

[22] Filed: Jun. 13, 1977

[51] Int. Cl.$^2$ .................... C07C 103/52; A61K 37/00
[52] U.S. Cl. .................. 260/112.5 LH; 260/112.5 R; 424/177
[58] Field of Search ............. 260/112.5 R, 112.5 LH; 424/177

[56] References Cited
PUBLICATIONS

D. H. Coy, et al., Mol. and Cellular Endocrinology 1976, pp. 201–208, 5.

Primary Examiner—Delbert R. Phillips
Attorney, Agent, or Firm—Stephen Raines; David B. Ehrlinger; Frank S. Chow

[57] ABSTRACT

New nonapeptides having the formula R-Trp-Ser(benzyl)-Tyr(benzyl)-D-Phe-Leu-Arg(X)-Pro-Gly-Y wherein X is a protective group, R is pGlu, protected His(benzyl), protected Ser(benzyl) or protected Cys(benzyl), and Y is lower alkoxy, amino, lower alkylamino or di(lower alkyl)amino.

3 Claims, No Drawings

NONAPEPTIDES AND METHODS FOR THEIR PRODUCTION

Summary and Detailed Description

The present invention relates to new peptide compounds that are useful as luteinizing hormone releasing factor antagonists and to methods for their production. More particularly, the invention relates to new nonapeptides that are represented by the formula R-Trp-Ser(benzyl)-Tyr(benzyl)-D-Phe-Leu-Arg(X)-Pro-Gly-Y

I wherein X is a protective group, preferably (4-methylphenyl)sulfonyl or nitro, R is pGlu, protected His(benzyl), protected Ser(benzyl) or protected Cys(benzyl), preferably where the protecting groups are t-butoxycarbonyl or benzyloxycarbonyl, and Y is lower alkoxy, amino, lower alkylamino or di(lower alkyl)amino.

The preferred compounds of formula I are those wherein X and R are as previously described, and Y is methoxy or amino.

In formula I, the conventional symbols for amino acid residues of peptide compounds linked thereto are used and each is intended to have the following meaning: Pro, D-prolyl or L-prolyl; His(benzyl), $N^{im}$-benzyl-D-histidyl or $N^{im}$-benzyl-L-histidyl; Trp, D-tryptophyl or L-tryptophyl; pGlu, D-pyroglutamyl or L-pyroglutamyl; Cys(benzyl), D-cysteinyl(benzyl) or L-cysteinyl(-benzyl); Leu, D-leucyl or L-leucyl; Arg, D-arginyl or L-arginyl; Gly, glycyl; Tyr(benzyl), D-tyrosyl(benzyl) or L-tyrosyl(benzyl); Ser(benzyl), D-seryl(benzyl) or L-seryl(benzyl); and D-Phe, D-phenylalanyl. In addition, the term "lower alkyl" is intended to mean a straight, branched or cyclic hydrocarbon moiety of up to 6 carbons atoms, such as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. A protective group is intended to mean a group usually employed in the area of peptides for protecting an amino function, such groups are disclosed in the following texts which are incorporated by reference: E. Schroder and K. Lubke, "The Peptides," Vol. I, Chapter 1., Academic Press, 1966 and J. Meienhofer in "Hormonal Proteins and Peptides," Vol. II, p. 227., Academic Press, 1973. These symbols and terms will also be used in the formulae that follow for other compounds and each such symbol or term should be understood to have the meaning given above.

In accordance with this invention, compounds of the formula I, wherein X and R are as previously defined and Y is lower alkoxy, are produced by removing a protected nonapeptide from a resin complex of the following structure R-Trp-Ser(benzyl)-Tyr(benzyl)-D-Phe-Leu-Arg(X)-Pro-Gly-resin

II wherein said resin is a resin employed in solid phase peptide syntheses, such as those disclosed in a text by Stewart and Young, "Solid Phase Peptide Synthesis," W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the nonapeptide through a methyleneoxy bridge wherein the methylene group is attached to the polymeric portion of the resin and the oxygen atom is attached to the non-apeptide and X and R are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 house to 4 days, preferably 16 to 24 hours, at about 15° C. to about 35° C.

While a large excess of the lower alkyl alcohol is preferred, only a catalytic amount of tertiary amine is required; however, larger amounts are preferred; such as about 10 percent volume/volume based on the amount of lower alkyl alcohol employed.

While it is not a preferred procedure, compounds of the formula I wherein Y is amino, lower alkylamino or di(lower alkyl)amino may be prepared by reacting compounds of the formula II wherein X and R are as previously defined, with ammonia, lower alkylamine or di(-lower alkyl)amine.

The resin complex is suspended in a solvent, such as methanol, ethanol, dimethylformamide, etc., at a temperature of from about 0° C. to 50° C. for periods of from 12 hours to 10 days. When employing less reactive amines, the preferred solvent is dimethylformamide.

The complex resins of the formula II are prepared by coupling a N-α-protected amino acid of the formula

R-OH

III with complex resins of the formula

Trp-Ser(benzyl)-Tyr-(benzyl)-D-Phe-Leu-Arg(X)-Pro-Gly-resin

IV wherein X and R are as previously defined in formula I, in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about 15 minutes to about 20 hours.

The complex resins of the formula IV are prepared by treating complex resins of the formula t-butoxycarbonyl-Trp-Ser(Benzyl)-Tyr(benzyl)-D-Phe-Leu-Arg(X)-Pro-Gly-resin

V wherein X is as previously defined in formula I with a large excess of trifluoroacetic acid utilizing dichloromethane as the solvent at temperatures of from 20° C. to 30° C. for about 10 minutes followed by neutralization of the trifluoroacetic acid salt with a base such as triethylamine.

The complex resins of the formula V are prepared by coupling t-butoxycarbonyl-Trp-OH to complex resins of the formula Ser(benzyl)-Tyr(benzyl)-D-Phe-Leu-Arg(X)-Pro-Gly-resin

VI wherein X is as previously defined in formula I using the reaction procedure described for the preparation of compounds of the formula II.

The complex resins of the formula VI are prepared by treating the complex resins of the formula t-butoxycarbonyl-Ser(benzyl)-Tyr(benzyl)-D-Phe-Leu-Arg(X)-Pro-Gly-resin

VII wherein X is as previously defined in formula I, with trifluoroacetic acid using the reaction procedure for the preparation of compounds of the formula IV.

The complex resins of the formula VII are prepared by coupling t-butoxycarbonyl-Ser(Benzyl)-OH to complex resins of the formula Tyr(benzyl)-D-Phe-Leu-Arg(X)-Pro-Gly-resin

VIII wherein X is as previously defined in formula I using the reaction procedure described for the preparation of compounds of the formula II.

The complex resins of the formula VIII are prepared by treating the complex resins of the formula t-butoxycarbonyl-Tyr(benzyl)-D-Phe-Leu-Arg(X)-Pro-Gly-resin

IX wherein X is as previously defined in formula I, with trifluoroacetic acid using the reaction procedure for the preparation of compounds of the formula IV.

The complex resins of the formula IX are prepared by coupling t-butoxycarbonyl-Tyr(benzyl)-OH to complex resins of the formula D-Phe-Leu-Arg(X)-Pro-Gly-resin

X wherein X is as previously defined in formula I according to the procedure used for the preparation of compounds of formula II.

The complex resins of the formula X are prepared by treating the complex resins of the formula t-butoxycarbonyl-D-Phe-Leu-Arg(X)-Pro-Gly-resin

XI wherein X is as previously defined in formula I with trifluoroacetic acid using the reaction procedure for the preparation of compounds of the formula IV.

The complex resins of the formula XI are prepared by coupling t-butoxycarbonyl-D-Phe-OH to complex resins of the formula Leu-Arg(X)-Pro-Gly-resin

XII wherein X is as previously defined in formula I, according to the procedure used for the preparation of compounds of formula II.

The complex resins of the formula XII are prepared by treating the complex resins of the formula t-butoxycarbonyl-Leu-Arg(X)-Pro-Gly-resin

XIII wherein X is as previously defined in formula I with trifluoroacetic acid using the reaction procedure for the preparation of compounds of the formula IV.

The complex resins of formula XIII are prepared by coupling t-butoxycarbonyl-Leu-OH to complex resins of the formula Arg(X)-Pro-Gly-resin

XIV wherein X is as previously defined in formula I according to the procedure used for the preparation of compounds of formula II.

The complex resins of the formula XIV are prepared by treating the complex resins of the formula t-butoxycarbonyl-Arg(X)-Pro-Gly-resin

XV wherein X is as previously defined in formula I, with trifluoroacetic acid using the reaction procedure for the preparation of compounds of formula IV.

The complex resins of formula XV are prepared by coupling t-butoxycarbonyl-Arg(X)-OH to a complex resin of the formula Pro-Gly-resin

XVI wherein X is as previously defined in formula I, according to the procedure used for the preparation of compounds of formula II.

The complex resins of the formula XVI are prepared by treating complex resins of the formula t-butoxycarbonyl-Pro-Gly-resin

XVII with trifluoroacetic acid using the reaction procedure for the preparation of compounds of formula IV.

The complex resins of the formula XVII are prepared by coupling t-butoxycarbonyl-Pro-OH to a complex resin of the formula Gly-resin according to the procedure used for the preparation of compounds of formula II.

In accordance with this invention, compounds of the formula I, wherein X and R are as previously described and Y is amino, lowr alkylamino or di(lower alkyl)amino are prepared by reacting a compound of the formula I wherein Y is alkoxy, preferably methoxy, with ammonia, lower alkylamine or di(lower alkyl)amine.

The reactions are conducted at temperatures of from about 5° C. to 100° C. for from 3 hours to 4 days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein X is a protective group inert to hydrazine and R is as previously defined and Y is amino, lower alkylamino or di(lower alkyl)amino are prepared by reacting a compound of the formula

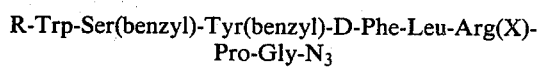

R-Trp-Ser(benzyl)-Tyr(benzyl)-D-Phe-Leu-Arg(X)-Pro-Gly-N₃

XVIII with ammonia, lower alkylamine or di(lower alkyl)amine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of the amine, about 10 percent, is preferred. When the protecting group, which is a portion of the R group is t-butoxycarbonyl, care should be taken to avoid the presence of a large excess of acid.

The azide compounds of the formula XVIII are normally prepared in situ by reacting a peptide hydrazide of the formula

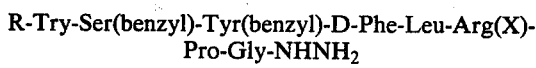

R-Try-Ser(benzyl)-Tyr(benzyl)-D-Phe-Leu-Arg(X)-Pro-Gly-NHNH₂

XIX wherein X is a protective group inert to hydrazine and R is as defined in formula I with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula XIX. The preparation of the azide is carried out at a temperature betweem −30° C. and 0° C. following the in situ formation of the azide of formula XVIII and prior to the further reaction of the peptide azide with the appropriate amine to form certain nonapeptides of formula I, a tertiary amine such as triethylamine is added to the reaction mixture to neutralize the acid used.

The compounds of formula XIX are prepared by reacting a compound of formula I wherein X is a protective group inert to hydrazine and Y is methoxy with hydrazine hydrate in methanol.

Compounds of the formula I wherein X and R are as described in formula I and Y is amino, lower alkylamino or di(lower alkyl)amino are prepared by coupling a compound of the formula

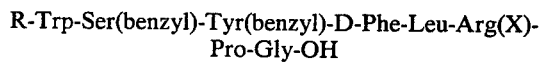

R-Trp-Ser(benzyl)-Tyr(benzyl)-D-Phe-Leu-Arg(X)-Pro-Gly-OH

XX with ammonia, a lower alkylamine or a di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° C. to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula XX are prepared by the hydrolysis of a compound of formula I wherein X and R are as previously defined in formula I and Y is lower alkoxy. The reaction is conducted at temperatures of from 20° C. to 30° C. using about 0.5 ml. of two normal aqueous sodium hydroxide solution and 10 ml. of solvent, usually water or an alcohol such as methanol, for each millimole of ester. The compound of formula XX is isolated after acidification with aqueous citric acid.

The compounds of this invention can exist in anhydrous forms as well as in solvated, including hydrated, forms. In general, the hydrated forms and the solvated forms with pharamceutically-acceptable solvents are equivalent to the anhydrous or unsolvated form for the purposes of the invention.

Nonapeptides of this invention were screened for LRF antagonist activity in vitro using rat anterior pituitary cell cultures as described by Vale et. al. [Endocrinology, 91, 562 (1972)]. The inhibition of LRF (luteinizing hormone releasing factor) induced luteinizing hormone (LH) release into the culture medium is the endpoint in this in vitro bioassay.

| ACTIVITY TABLE FOR IN VITRO TEST IN RAT ANTERIOR PITUITARY CELL CULTURES | | | |
|---|---|---|---|
| Compound | Molar Conc. | LH Valve ng./ml. | % LH Release Inhibition |
| L-Pyroglutamyl-L-tryptophyl-O-benzyl-L-seryl-O-benzyl-L-tyrosyl-D-phenyl-alanyl-L-leucyl-N^G-[(4-methylphenyl)-sulfonyl]-L-arginyl-L-prolyl-glycinamide | 1×10⁻⁷ | 22.65 | 90 |
| LRF Control | 5×10⁻¹⁰ | 80.93 | |
| Saline Control | | 16.22 | |
| N^α-t-Butoxycarbonyl-N^im-benzyl-L-histidyl-L-tryptophyl-O-benzyl-L-seryl-O-benzyl-L-tyrosyl-D-phenyl-alanyl-L-leucyl-N^G-[(4-methylphenyl)-sulfonyl]-L-arginyl-L-prolyl- | 1×10⁻⁷ | 24.91 | 87 |

-continued

ACTIVITY TABLE FOR IN VITRO TEST IN RAT ANTERIOR PITUITARY CELL CULTURES

| Compound | Molar Conc. | LH Valve ng./ml. | % LH Release Inhibition |
|---|---|---|---|
| glycinamide | $1 \times 10^{-8}$ | 52.47 | 44 |
| LRF Control | $5 \times 10^{-10}$ | 80.93 | |
| Saline Control | | 16.22 | |
| $N^\alpha$-t-Butoxycarbonyl-O-benzyl-L-seryl-L-tryptophyl-O-benzyl-L-seryl-O-benzyl-L-tyrosyl-D-phenylalanyl-L-leucyl-$N^G$-nitro-L-arginyl-L-prolyl-glycinamide | $1 \times 10^{-7}$ $1 \times 10^{-8}$ | 15.65 43.88 | 101 57 |
| LRF Control | $5 \times 10^{-10}$ | 80.93 | |
| Saline Control | | 16.22 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the nonapeptides of this invention are useful in controlling ovulation and in restricting fertility.

The invention is illustrated by the following examples.

EXAMPLE 1

L-Pyroglutamyl-L-tryptophyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine resin, 8.5 g., is treated with methanol, 100 ml. and triethylamine, 10 ml. at room temperature for 3 days, filtered and the filtrate evaporated. The crude product is chromatographed on silica gel with methanol-benzene (1:4) to give 2.0 g. of L-pyroglutamyl-L-tryptophyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine methyl ester containing 2½ moles of water of hydration; m.p. 115°–120° C.

The L-pyroglutamyl-L-tryptophyl-O-benzyl-L-seryl-O-benzyl-L-tyrosyl-D-phenylalanyl-L-leucyl-$N^G$-[(4-methylphenyl)sulfonyl]-L-arginly-L-prolyl-glycine resin is obtained from 28.3 g. of $N^\alpha$-t-butoxycarbonyl-glycine resin by successive couplings, according to the General Procedure given below, of 1) 5.8 g., 0.027 mol., of $N^\alpha$-t-butoxycarbonyl-L-proline and 5.6 g., 0.027 mol., of dicyclohexylcarbodiimide, 2) 11.6 g., 0.027 mol., of $N^\alpha$-t-butoxycarbonyl-$N^G$-[(4-methylphenyl)sulfonyl]-L-arginine and 5.6 g., 0.027 mol., of dicyclohexylcarbodiimide, 3) 6.2 g., 0.027 mol., of $N^\alpha$-t-butoxycarbonyl-L-leucine and 5.6 g., 0.027 mol., of dicyclohexylcarbodiimide, 4) 7.2 g., 0.027 mol., of $N^\alpha$-t-butoxycarbonyl-D-phenylalanine and 5.6 g., 0.027 mol., of dicyclohexylcarbodiimide, 5) 10 g., 0.027 mol., of $N^\alpha$-t-butoxycarbonyl-O-benzyl-L-tyrosine and 5.6 g., 0.027 mol., of dicyclohexylcarbodiimide, 6) 8 g., 0.027 mol., of $N^\alpha$-t-butoxycarbonyl-O-benzyl-L-serine and 5.6 g., 0.027 mol., of dicyclohexylcarbodiimide, 7) 8.2 g., 0.027 mol., of $N^\alpha$-t-butoxycarbonyl-L-tryptophan and 5.6 g., 0.027 mol., of dicyclohexylcarbodiimide, 8) 8.75 g. of the resin obtained in step 7 was reacted with 0.9 g., 0.007 mol., of L-pyroglutamic acid and 1.5 g., 0.007 mol., of dicyclohexylcarbodiimide.

$N^\alpha$-t-Butoxycarbonyl-glycine resin is obtained by refluxing 100 g., 0.116 mol., of 1% chloromethylated resin, 22.3 g., 0.13 mol., of $N^\alpha$-t-butoxycarbonyl-glycine and 12.9 g., 0.13 mol., of triethylamine in 500 ml. of absolute ethanol for four days; 104.3 g. Nitrogen analysis shows 0.00063 mol. per gram.

General Procedure for the Solid Phase Synthesis of Peptide Resins

The peptide resin is obtained by attaching an α-amino-protected amino acid to a resin (usually a chloromethylated resin which is commercially available from Lab Systems, Inc., San Mateo, California). The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart, "Solid Phase Peptide Synthesis," W. H. Freeman and Co., 1969.

Each cycle of the procedure follows the scheme:
1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. 15 to 30 minutes agitation with the α-amino-protected amino acid which is present in up to a fourfold molar excess based on the resin nitrogen analysis. However, when a large excess of the α-amino-protected amino acid is used it is agitated with the resin for fifteen minutes and the excess recovered by draining the solution from the reactor.
6. Addition of dicyclohexylcarbodiimide at least equivalent to the α-amino-protected amino acid in Step 5 in dichloromethane followed by agitation for 4 to 20 hours. In the alternate method, a 3.3-fold excess of dicyclohexylcarbodiimide is used relative to the α-amino-protected amino acid resin.
7. Three washes with dichloromethane.

EXAMPLE 2

The methyl ester of Example 1, 0.3 g., is treated with 100 ml. of methanol saturated with ammonia for 8 days at 25° C. The product, L-pyroglutamyl-L-tryptophyl-O-benzyl-L-seryl-O-benzyl-L-tyrosyl-D-phenylalanyl- L-leucyl-N$^G$-[(4-methylphenyl)sulfonyl]-L-arginyl-L-prolyl-glycinamide, 0.2 g., is obtained as a hydrate after evaporation and chromatography on silica gel using methanol-benzene (1:9); m.p. 138–143° C.

EXAMPLE 3

N$^\alpha$-t-Butoxycarbonyl-N$^{im}$-benzyl-L-histidyl-L-tryptophyl-O-benzyl-L-seryl-O-benzyl-L-tyrpsyl-D-phenylalanyl-L-leucyl-N$^G$-[(4-methylphenyl)sulfonyl]-L-arginyl-L-prolyl-glycine methyl ester, 0.3 g., is treated with 100 ml. of methanol saturated with ammonia for 8 days at 25° C. The product, N$^\alpha$-t-butoxycarbonyl-N$^{im}$-benzyl-L-histidyl-L-tryptophyl-O-benzyl-L-seryl-O-benzyl-L-tyrosyl-D-phenylalanyl-L-leucyl-N$^G$-[(4-methylphenyl)sulfonyl]-L-arginyl-L-prolyl-glycinamide, 0.2 g., is obtained as a hydrate after evaporation and chromatography on silica gel using methanol-benzene (1:9); m.p. 119°–124° C.

N$^\alpha$-t-Butoxycarbonyl-N$^{im}$-benzyl-L-histidyl-L-tryptophyl-O-benzyl-L-seryl-O-benzyl-L-tyrosyl-D-phenylalanyl-L-leucyl-N$^G$-[(4-methylphenyl)sulfonyl]-L-arginyl-L-prolyl-glycine resin, 9.2 g., is treated with methanol, 100 ml. and triethylamine, 10 ml. at room temperature for 3 days, filtered and the filtrate evaporated. The crude product is chromatographed on silica gel with methanol-benzene (1:4) to give 3.0 g. of N$^\alpha$-t-butoxycarbonyl-N$^{im}$-benzyl-L-histidyl-L-tryptophyl-O-benzyl-L-seryl-O-benzyl-L-tyrosyl-D-phenylalanyl-L-leucyl-N$^G$-[(4-methylphenyl)sulfonyl]-L-arginyl-L-prolyl-glycine methyl ester, in the form of its sesquihydrate; m.p. 95°–100° C.

N$^\alpha$-t-Butoxycarbonyl-N$^{im}$-benzyl-L-histidyl-L-tryptophyl-O-benzyl-L-seryl-O-benzyl-L-tyrosyl-D-phenylalanyl-L-leucyl-N$^G$-[(4-methylphenyl)sulfonyl]-L-arginyl-L-prolyl-glycine resin is obtained according to the General Procedure of Example 1 except that 2.4 g., 0.007 mol., of N$^\alpha$-t-butoxycarbonyl-N$^{im}$-benzyl-L-histidine and 1.5 g., 0.007 mol., of dicyclohexylcarbodiimide are used in place of the L-pyroglutamic acid.

EXAMPLE 4

N$^\alpha$-t-Butoxycarbonyl-O-benzyl-L-seryl-L-tryptophyl-O-benzyl-L-seryl-O-benzyl-L-tyrosyl-D-phenylalanyl-L-leucyl-N$^G$-nitro-L-arginyl-L-prolyl-glycine resin, 14.6 g., is suspended in 300 ml. of methanol saturated with ammonia while the mixture is cooled in an ice bath. The suspension is warmed slightly, stoppered and stirred for 3 days, filtered and the solvents evaporated to give 0.31 g. of N$^\alpha$-t-butoxycarbonyl-O-benzyl-L-seryl-L-tryptophyl-O-benzyl-L-seryl-O-benzyl-L-tyrosyl-D-phenylalanyl-L-leucyl-N$^G$-nitro-L-arginyl-L-prolyl-glycinamide after chromatography over silica gel using methanol-chloroform (1:9); m.p. 120°–142° C; $[\alpha]_D$ −30.4° (c 1.02, dimethylformamide).

N$^\alpha$-t-Butoxycarbonyl-O-benzyl-L-seryl-L-tryptophyl-O-benzyl-L-seryl-O-benzyl-L-tyrosyl-D-phenylalanyl-L-leucyl-N$^G$-nitro-L-arginyl-L-prolyl-glycine resin is obtained by using the General Procedure of Example 1, employing 50 g., 0.0328 mol., of N$^\alpha$t-butoxycarbonyl-glycine resin with 1) 7.06 g., 0.0328 mol., of N$^\alpha$-t-butoxycarbonyl-L-proline and 6.76 g., 0.0328 mol., of dicyclohexylcarbodiimide, 2) 10.4 g., 0.0328 mol., of N$^\alpha$-t-butoxycarbonyl-N$^G$-nitro-L-arginine and 6.76 g., 0.0328 mol., of dicyclohexylcarbodiimide, 3) 7.6 g., 0.03 mol., of N$^\alpha$-t-butoxycarbonyl-L-leucine hydrate and 6.76 g., 0.0328 mol., of dicyclohexylcarbodiimide, 4) using 4/5th of the resin obtained in step 3 with 6.96 g., 0.0263 mol., of N$^\alpha$-t-butoxycarbonyl-D-phenylalanine and 5.41 g., 0.0263 mol., of dicyclohexylcarbodiimide, 5) 9.8 g., 0.0263 mol., of N$^\alpha$-t-butoxycarbonyl-O-benzyl-L-tyrosine and 5.41 g., 0.0263 mol., of dicyclohexylcarbodiimide, 6) 8.1 g., 0.0263 mol., of N$^\alpha$-t-butoxycarbonyl-O-benzyl-L-serine and 5.41 g., 0.0263 mol., of dicyclohexylcarbodiimide; a second coupling is performed with 4.0 g., 0.0131 mol., of N$^\alpha$-t-butoxycarbonyl-O-benzyl-L-serine and 2.7 g., 0.0131 mol., of dicyclohexylcarbodiimide, 7) 8.0 g., 0.0263 mol., of N$^\alpha$-t-butoxycarbonyl-L-tryptophan and 5.41 g., 0.0263 mol., of dicyclohexylcarbodiimide, 8) using 15 g. of the resin obtained in step 7 with 2.0 g., 0.0066 mol., of N$^\alpha$-t-butoxycarbonyl-O-benzyl-L-serine and 1.3 g., 0.0063 mol. of dicyclohexylcarbodiimide.

N$^\alpha$-t-Butoxycarbonyl-glycine resin is obtained by refluxing 100 g., 0.116 mol., of 1% chloromethylated resin, 23.8 g., 0.138 mol., of N$^\alpha$-t-butoxycarbonyl-glycine and 13 g., 0.129 mol., of triethylamine in 400 ml. of absolute ethanol for two days. Nitrogen analysis shows 0.00066 mol. per gram.

EXAMPLE 5

L-Pyroglutamyl-L-tryptophyl-O-benzyl-L-seryl-O-benzyl-L-tyrosyl-D-phenylalanyl-L-leucyl-N$^G$-nitro-L-arginyl-L-prolylglycine resin, 15.3 g., is suspended in 300 ml. of methanol saturated with ammonia while the mixture is cooled in an ice bath. The suspension is warmed slightly, stoppered and stirred at room temperature for three days, filtered and the solvents evaporated to give 0.3 g. of L-pyroglutamyl-L-tryptophyl-O-benzyl-L-seryl-O-benzyl-L-tyrosyl-D-phenylalanyl-L-leucyl-N$^G$-nitro-L-arginyl-L-prolyl-glycinamide as a dihydrate after chromatography over silica gel using methanol-chloroform (15:85); m.p. 135°–163° C; $[\alpha]_D^{23}$ −33° (c 1.03, dimethylformamide).

L-Pyroglutamyl-L-tryptophyl-O-benzyl-L-seryl-O-benzyl-L-tyrosyl-D-phenylalanyl-L-leucyl-N$^G$-nitro-L-arginyl-L-prolylglycine resin is obtained according to the General Procedure of Example 4 except that 0.84 g., 0.0065 mol., of L-pyroglutamic acid and 1.3 g., 0.0063 mol., of dicyclohexylcarbodiimide are used in place of N$^\alpha$-t-butoxycarbonyl-O-benzyl-L-serine in step 8.

EXAMPLE 6

N$^\alpha$-t-Butoxycarbonyl-S-benzyl-L-cysteinyl-L-tryptophyl-O-benzyl-L-seryl-O-benzyl-L-tyrosyl-D-phenylalanyl-L-leucyl-N$^G$-nitro-L-arginyl-L-prolyl-glycine resin, 14.4 g., is suspended in 300 ml. of methanol saturated with ammonia while the mixture is cooled in an ice bath. The suspension is warmed slightly, stoppered and stirred at room temperature for two days, filtered and the solvents evaporated to give 0.43 g. of N$^\alpha$-t-butoxycarbonyl-S-benzyl-L-cysteinyl-L-tryptophyl-O-benzyl-L-seryl-O-benzyl-L-tyrosyl-D-phenylalanyl-L-leucyl-N$^G$-nitro-L-arginyl-L-prolyl-glycinamide as a hydrate after chromatography over silica gel using methanol-chloroform (1:19); m.p. 123°–142° C; $[\alpha]_D^{23}$ −33° (c 1.01, dimethylformamide).

N$^\alpha$-t-Butoxycarbonyl-S-benzyl-L-cysteinyl-L-tryptophyl-O-benzyl-L-seryl-O-benzyl-L-tyrosyl-D-phenylalanyl-L-leucyl-N$^G$-nitro-L-arginyl-L-prolyl-glycine resin is obtained by using the General Procedure of Example 1, employing 50 g., 0.031 mol., of N$^\alpha$-t-butoxycarbonyl-glycine resin with 1) 7.16 g., 0.033 mol., of N$^\alpha$-t-butoxycarbonyl-L-proline and 7.0 g., 0.034 mol., of dicyclohexylcarbodiimide; a second coupling is performed with 4.0 g., 0.0186 mol., of N$^\alpha$-t-butoxycarbonyl-L-proline and 4.4 g., 0.0214 mol., of dicyclohexylcarbodiimide, 2) 9.9 g., 0.031 mol., of $N^\alpha$-t-butoxycarbonyl-$N^G$-nitro-L-arginine and 7.0 g., 0.034 mol., of dicyclohexylcarbodiimide, 3) 7.8 g., 0.031 mol., of $N^\alpha$-t-butoxycarbonyl-L-leucine hydrate and 7.0 g., 0.034 mol., of dicyclohexylcarbodiimide, 4) 8.3 g., 0.031 mol., of $N^\alpha$-t-butoxycarbonyl-D-phenylalanine and 7.0 g., 0.034 mol., of dicyclohexylcarbodiimide, 5) 12.3 g., 0.033 mol., of $N^\alpha$-t-butoxycarbonyl-O-benzyl-L-tyrosine and 7.0 g., 0.034 mol., of dicyclohexylcarbondiimide, 6) 10.1 g., 0.033 mol., of $N^\alpha$-t-butoxycarbonyl-O-benzyl-L-serine and 7.0 g., 0.034 mol., of dicyclohexylcarbodiimide, 7) 10.1 g., 0.033 mol., of $N^\alpha$-t-butoxycarbonyl-L-tryptophan and 7.0 g., 0.034 mol.,, of dicyclohexylcarbodiimide; a second coupling is performed with 5.0 g., 0.0164 mol., of $N^\alpha$-t-butoxycarbonyl-L-tryptophan and 3.5 g., 0.017 mol., of dicyclohexylcarbodiimide; a third coupling is performed with 5.0 g., 0.0164 mol., of $N^\alpha$-t-butoxycarbonyl-L-tryptophan and 3.5 g., 0.0170 mol., of dicyclohexylcarbodiimide, 8) using 14 g. of the resin obtained in step 7 with 2.1 g., 0.068 mol., of $N^\alpha$-t-butoxycarbonyl-S-benzyl-L-cysteine and 1.3 g., 0.0063 mol., of dicyclohexylcarbodiimide.

$N^\alpha$-t-Butoxycarbonyl-glycine resin is obtained by refluxing 100 g., 0.116 mol., of 1% chloromethylated resin, 25 g., 0.143 mol., of $N^\alpha$-t-butoxycarbonyl-glycine and 13 g., 0.129 mol., of triethylamine in 400 ml. of absolute ethanol for 2 days. Nitrogen analysis shows 0.00062 mol. per gram.

We claim:

1. A nonapeptide having the name $N^\alpha$-t-butoxycarbonyl-$N^{im}$-benzyl-L-histidyl-L-tryptophyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycinamide.

2. A nonapeptide having the name $N^\alpha$-t-butoxycarbonyl-O-benzyl-L-seryl-L-tryptophyl-O-benzyl-L-seryl-O-benzyl-L-tyrosyl-D-phenylalanyl-L-leucyl-$N^G$-nitro-L-arginyl-L-propyl-glycinamide.

3. A compound having the name L-pyroglutamyl-L-tryptophyl-O-benzyl-L-seryl-O-benzyl-L-tyrosyl-D-phenylalanyl-L-leucyl-$N^G$-(4-methylphenyl)sulfonyl-L-arginyl-L-prolyl-glycine methyl ester.

* * * * *